United States Patent [19]

Gershuny

[11] 4,401,117

[45] Aug. 30, 1983

[54] THERAPEUTIC APPLIANCE

[76] Inventor: Hyman Gershuny, 70 Highland Ave., Newport, Vt. 05855

[21] Appl. No.: 236,707

[22] Filed: Feb. 23, 1981

[51] Int. Cl.[3] ...................... A61M 15/08; A62B 23/06

[52] U.S. Cl. ........................... 128/206.11; 128/203.22

[58] Field of Search ...................... 128/206.11, 203.22, 128/151, 296, 263, 342, 325

[56] References Cited

U.S. PATENT DOCUMENTS

| | | | |
|---|---|---|---|
| 2,660,166 | 11/1953 | Coleman | 128/206.11 X |
| 2,968,858 | 1/1961 | Brenner et al. | 128/296 X |
| 4,159,719 | 7/1979 | Haerr | 128/151 X |
| 4,221,217 | 9/1980 | Amezcua | 128/203.22 X |

*Primary Examiner*—Henry J. Recla

[57] ABSTRACT

A measured amount of fibrous material, preferably in the form of a rolled up strip, is placed in each nostril to aid the cilia of the nose in their filtering function for the air entering the lungs. The aid thus given the nasal cilia can improve their filtering function by more than 100%, and become a substantial factor in preventing or curing all kinds of respiratory disease in a polluted environment. The fit of the appliance and the amount of filtration can be controlled by the length and thickness of the strip.

2 Claims, 3 Drawing Figures

THERAPEUTIC APPLIANCE

BACKGROUND OF THE INVENTION

This invention relates to therapeutic appliances, particularly filters and medication used in and inhaled through the nose. Presently, many diseases of the respiratory tract are treated by medicines ingested orally or through a spray into the nasal and bronchial tubes. These medicines may or may not be effective, and some may be downright harmful, with numerous known and unknown side effects.

It stands to reason, and most will probably agree, that if a way can be found to reduce or eliminate germs, viruses, and other noxious substances from the air we breathe, there will be found a reduced or no necessity for cold remedies, inhalants, flu shots antibiotics for air borne germs, etc. and the diseases, discomforts, and inconveniences they are supposed to allay. Our natural gift of the nasal and bronchial cilia have now become greatly handicapped in our grossly polluted civilization.

The prior art has provided a variety of nasal filters to filter incoming air and supply medication, but most people can plainly see that they are not widely used, for reasons that the invention herein corrects, in order to produce an economical, practical, viable, and functionally effective appliance. Among the drawbacks of prior art filters is they generally are visible to casual observers (thus making the user feel self-conscious) and they are not adjustable to accommodate different size nasal passages.

SUMMARY OF THE INVENTION

In accordance with one preferred embodiment of my invention, a nasal filter is formed by rolling up a flat strip of fuzzy material to form a cylinder, which is inserted into one or both nostrils. If desired, these strips can be exposed to medicinal or aromatic vapors, which will be absorbed by the material and inhaled when the strip is used as a filter, and exhaled when used as a deodorant. Likewise, particles of adsorbent material like chlorophyll or carbon granules, but not restricted to these, could be interspersed among the fibers to adsorb noxious gases, and prevent their entry into the respiratory system.

The simplicity of my invention permits the filter to be inserted into the nostril so that it will not show when worn. When removal is desired it can be either blown out into a handkerchief, or grasped and pulled out by a pair of inexpensive tongs or tweezers that would be included in the commercial package sold retail. A third method for removal could be to affix a colorless transparent plastic string which will always be available just about outside the nostril, to be grasped by the fingers and the appliance pulled out.

The effectiveness and comfort of the filter can be very easily regulated by the manufacturer or user by changing the quantity of the fuzzy material in the strip, by varying the thickness of the material, or by varying the length or width of the strip. Thus different sizes of nasal filters can be arranged to accommodate different sized nasal passages. Also, the tightness of fit will serve to control the amount of filtration attained.

A major advantage of the nasal filter described herein is that it is readily adaptable to accommodate all sizes of nasal passages. Among its other advantages are that it can be discarded and replenished economically, and it can be worn all day while the wearer goes about his or her daily affairs without embarrassment. It never need be conspicuous or obvious such as compelled by the previous state of the art.

BRIEF DESCRIPTION OF THE DRAWINGS

In the accompanying drawings, forming a material part of this disclosure.

DETAILED DESCRIPTION

The nasal filter of this invention uses a measured volume of fuzzy fibrous material which is neither too large to block the passage of air through the user's nasal passages, nor too small to substantially reduce the air filtering capacity of said nasal filter. A preferred embodiment of my invention uses a flat strip of soft fuzzy material such as absorbent cotton or any other fine fibrous material, whether natural or artificial, as shown in FIG. 1.

Figure 1:
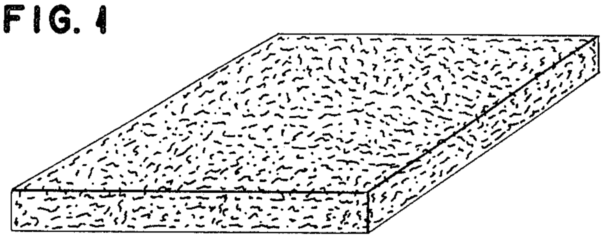
FIG. 1 is a view of a strip that may be used for this invention.
Figure 2:
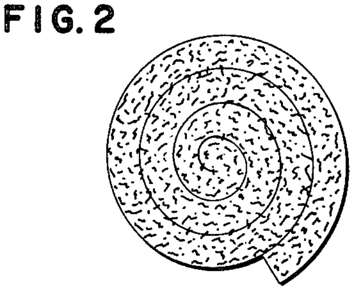
FIG. 2 is a cross-sectional view of a strip such as that shown in FIG. 1, rolled into a cylinder.

FIG. 2 shows a cross-sectional view of the strip in FIG. 1 rolled up into the form of a cylinder, to be placed into a nostril so that the air coming through said nostril will be contacted by the disoriented fibers in the strip for removal of a maximal amount of dust particles and germs polluting the air, with a minimal amount of extra breathing effort. Particles of gas adsorbing material may be dispersed throughout its volume, to prevent noxious and odoriferous gases from entering the respiratory system. Also, the strip of fuzzy material can be provided in any way with an aura of medicinal or perfumed vapor surrounding it.

Figure 3:
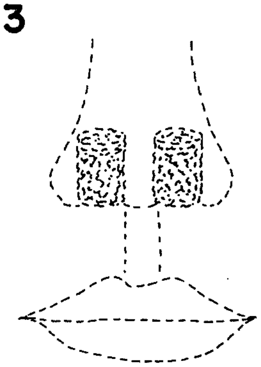
FIG. 3 shows a nasal filter in place in each nostril in a person's nose.

FIG. 3 shows the air filter described herein in each nostril of a person's nose.

The material herein, whether employing reinforcing or "backing" material, or used by itself to help the work of the nasal cilia, can be arranged so that its fibers will intermingle with the nasal hair to provide an opportunity for mucous to form and be absorbed by said filter, if necessary to the therapeutic process, and a means for keeping said filter in place. Its capacity to absorb the mucous is therefore increased so that the use of a handkerchief will be minimized until a fresh filter replaces the soaked one. A backing strip supporting the fuzzy material can be used if desired. However, a filter without any backing might be preferable in that such backing might permit the nasal filter to slip out of the nostril prematurely when wet with mucous. Removal of the used disposable filter will be no problem. For example, several suggestions in the above "Summary of the Invention" are presented.

As mentioned above, the fit of the nasal filter can be altered simply by changing the length of the original strip of material. The natural springiness of the material, as it tries to unwind from its cylindrical roll, will tend to help hold the filter in the nostril. The length of the strip will affect the diameter of the cylinder which results from rolling it up, thus affecting the manner in which it will fit into a nasal passage. Also, for a nasal passage of a given size, the length of the starting strip will affect the tightness of the rolled up cylinder of material. This in turn will affect the efficiency of the resulting filter as well as the ease or difficulty of breathing with the filter in place. When this filter is used in a situation in which very small particles must be filtered out, it would be advantageous to start with a relatively long strip of material to achieve a tight efficient filter. In order to accommodate those people who wish to utilize the filter in different situations and for different members of the family, it might be advantageous to provide the material in the form of a continuous roll so that the user may cut off strips of appropriate length for each different circumstance.

Although the preferred embodiment of my invention utilizes a strip of material that is wound only around itself, it will be understood by those skilled in the art that the material could be wound around a core which might contain for example a medication of some kind.

Those skilled in the art will also recognize that various medications and/or fragrances can be incorporated within the material, or can be placed therein by a user. Additionally, the filtering action of the material could be enhanced by the use of an adsorbant such as charcoal dispersed through it. Such dispersal would preferably be manufactured into the fuzzy material.

While I have illustrated and described the preferred embodiments of my invention, it is to be understood that I do not limit myself to the constructions herein disclosed, and the right is reserved to all changes and modifications coming within the scope of the invention as defined in the appended claims.

Having thus described my invention, what I claim is new, and desire to secure by Letters Patent is:

1. A therapeutic appliance useful as a nasal filter comprising:

a substantially rectangular strip of material capable of trapping air-borne pollutants, said material having a stronger material backing, said material being rolled into a substantially cylindrical shape to be held in the nostril of a user, the volume of said shape being substantially filled by said material so that substantially all of the air passing through the nose of the user will pass through said material, the springiness of the material enhancing its ability to stay in said nostril; and particles of gas adsorbent material interspersed within said material to retard and prevent the passage of outside noxious gases through and beyond the nasal passages into the bronchial tubes and lungs.

2. A therapeutic appliance to be used as an important aid to the function of the cilia of the nasal passages, comprising:

a substantially rectangular strip of material with a stronger material backing, said strip containing a measured amount of fuzzy material consisting of fine fibers oriented in random directions, being rolled in order to fit into the nostrils of the user, its fibers to mingle with the cilia of the nose, thereby retarding and filtering out air-borne pollutants, or retarding the flow of blood in the event of nose bleed; and particles of gas adsorbent material interspersed among said fibers to retard and prevent the passage of outside noxious gases through and beyond the nasal passages into the bronchial tubes and lungs.

* * * * *